United States Patent [19]
Merich

[11] Patent Number: 6,146,639
[45] Date of Patent: Nov. 14, 2000

[54] ARTHRITIS, MUSCLE PAIN, AND DRY SKIN REMEDY

[76] Inventor: Nick Merich, deceased, late of Daytona Beach, Fla., by Nikolas Merich, heir

[21] Appl. No.: 09/360,797

[22] Filed: Jul. 26, 1999

[51] Int. Cl.$^7$ .............................. A61K 35/78; A61K 9/00
[52] U.S. Cl. ........................................ 424/195.1; 424/400
[58] Field of Search .................................. 424/720, 400, 424/195.1; 514/171, 944

[56] References Cited

U.S. PATENT DOCUMENTS

| | | | |
|---|---|---|---|
| 3,852,454 | 12/1974 | Jaffe | 514/345 |
| 3,928,599 | 12/1975 | Sullivan | 514/456 |
| 3,995,030 | 11/1976 | Malachowski | 424/600 |
| 4,176,179 | 11/1979 | Gainer | 514/53 |
| 4,218,449 | 8/1980 | Wyburn-Mason | 514/235.8 |
| 4,271,154 | 6/1981 | Richards | 424/195.1 |
| 4,387,093 | 6/1983 | Lysaght | 424/131 |
| 4,402,965 | 9/1983 | Wyburn-Mason | 424/272 |
| 4,426,384 | 1/1984 | Wyburn-Mason | 424/253 |
| 4,468,393 | 8/1984 | Geschickter | 424/245 |
| 4,552,762 | 11/1985 | Nepon | 424/106 |
| 4,628,052 | 12/1986 | Peat | 514/171 |
| 4,767,626 | 8/1988 | Cheng | 424/195.1 |
| 4,898,884 | 2/1990 | Watson | 514/553 |
| 4,963,591 | 10/1990 | Fourman et al. | 514/944 |
| 4,968,510 | 11/1990 | Jensen | 424/630 |
| 5,032,613 | 7/1991 | Watson | 514/553 |
| 5,073,366 | 12/1991 | Beck | 424/720 |
| 5,145,837 | 9/1992 | Feyen et al. | 514/16 |
| 5,658,580 | 8/1997 | Mausner | 424/401 |
| 5,683,698 | 11/1997 | Chavali et al. | 424/195.1 |
| 5,716,646 | 2/1998 | Smith et al. | 424/646 |
| 5,723,503 | 3/1998 | Smith et al. | 514/825 |
| 5,750,144 | 5/1998 | Moore | 424/451 |
| 5,827,886 | 10/1998 | Hersh | 514/562 |
| 5,855,888 | 1/1999 | Nishida et al. | 424/156.1 |

*Primary Examiner*—David M. Naff
*Assistant Examiner*—Michael V. Meller
*Attorney, Agent, or Firm*—Paul S. Rooy

[57] ABSTRACT

An arthritis, muscle pain, and dry skin remedy is provided containing rubbing alcohol, witch hazel, and olive oil. In the preferred embodiment, the remedy contains sixteen parts rubbing alcohol, sixteen parts witch hazel, and four parts olive oil. An alternate embodiment arthritis, muscle pain, and dry skin remedy is also disclosed which relieves symptoms of muscle pain, arthritis, and dry, scaly skin in horses. This alternate remedy uses castor oil instead of olive oil.

5 Claims, 2 Drawing Sheets

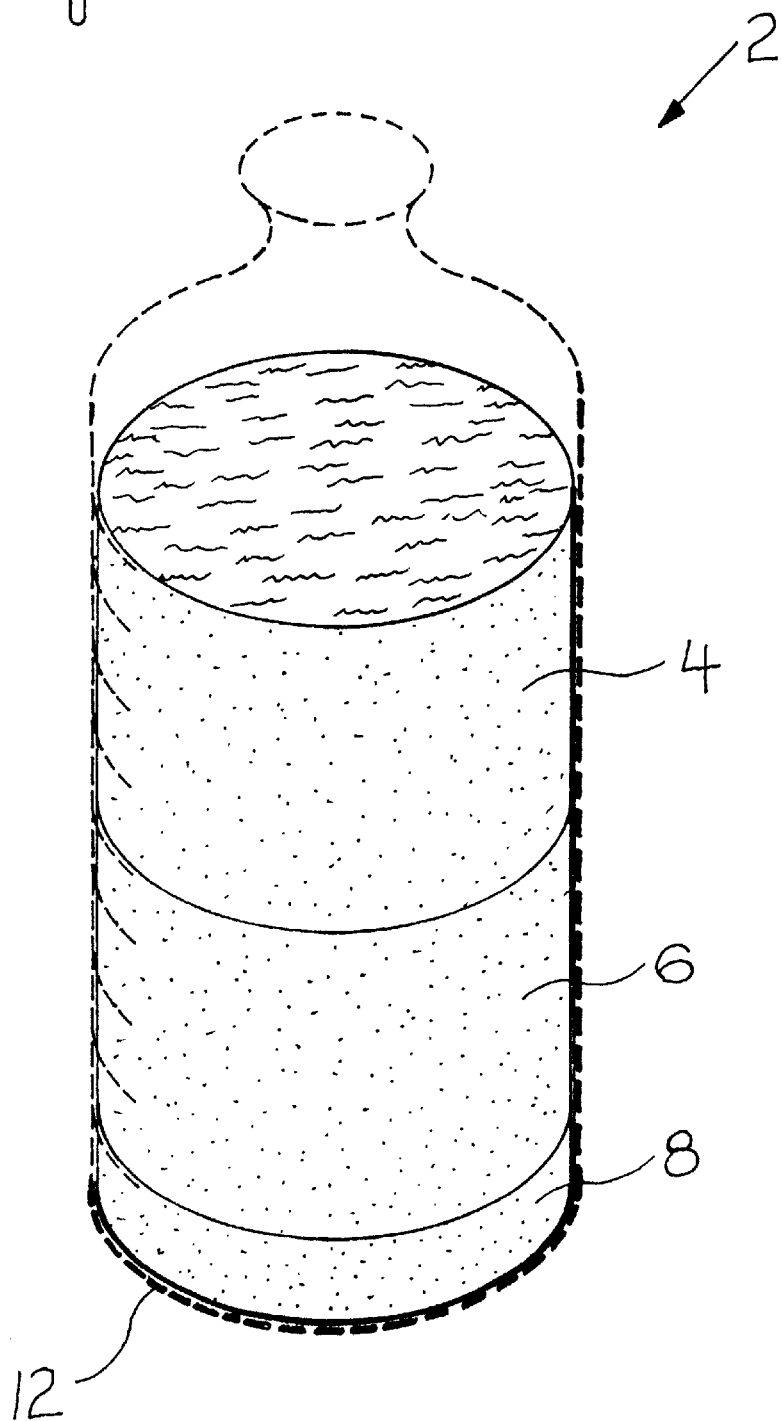

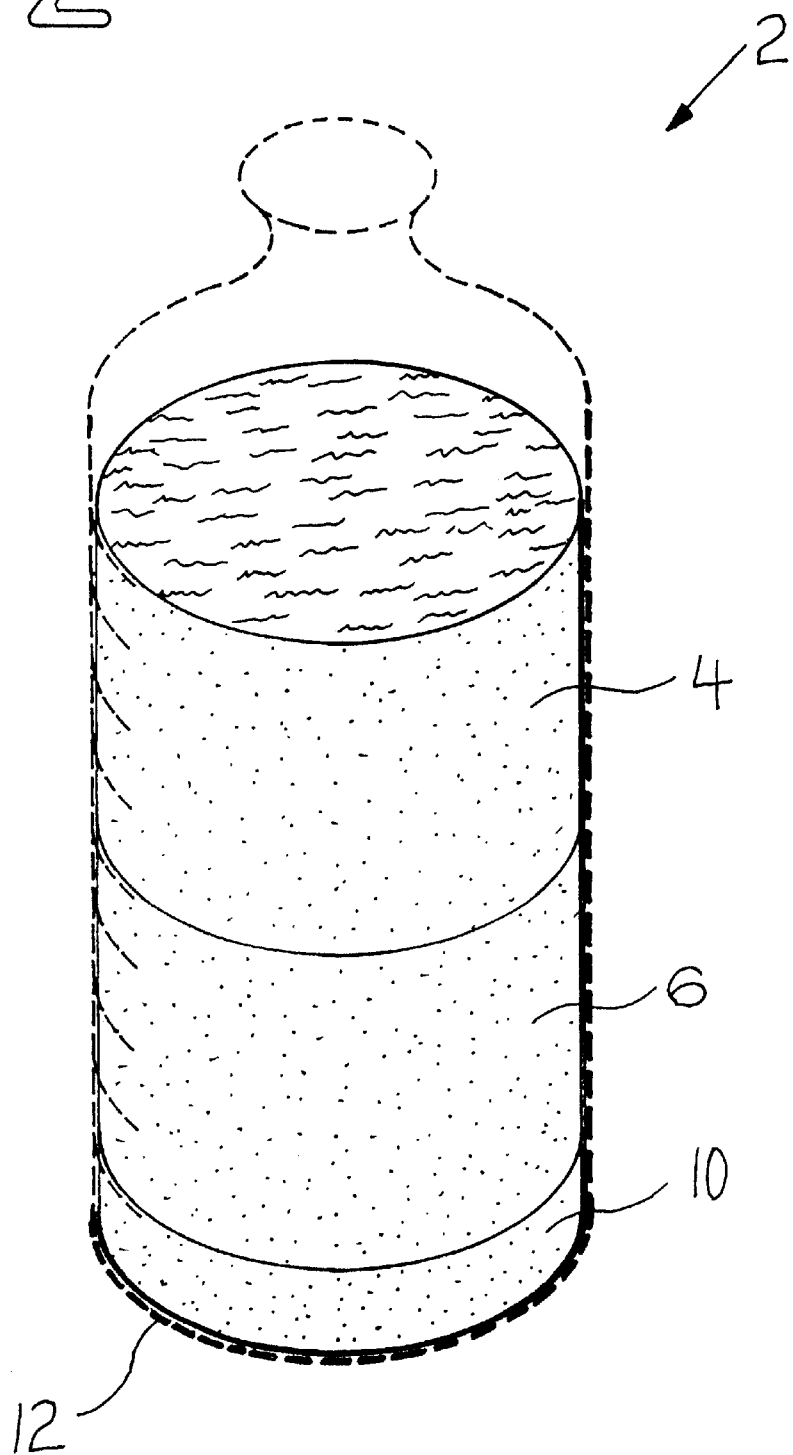

ARTHRITIS, MUSCLE PAIN, AND DRY SKIN REMEDY

BACKGROUND OF THE INVENTION

1. Field of the Invention

This invention relates to arthritis remedies, and in particular to an arthritis and muscle pain remedy which also treats dry or scaly skin.

2. Background of the Invention

Arthritis is a term which refers to a group of diseases which affect the joint. Symptoms of arthritis include pain, stiffness and swelling of the affected joints. The disease is a serious problem in that it is very widely spread. For example, in the United States alone more than 31 million individuals suffer from arthritis. The two main types of arthritis are osteoarthritis and rheumatoid arthritis.

Osteoarthritis is also referred to as degenerative joint disease, and occurs where the joint itself wears out. This strain of arthritis is common in elderly people, and it may also occur where a joint has been injured repeatedly. The most commonly affected joints are in the hands, knees, lower back and neck.

Patients afflicted with this type of arthritis suffer pain in the affected area, and may also feel a grating sensation when the joint is flexed. In this variety of arthritis, the cartilage between the bones breaks down, causing the bones to rub against each other. The characteristic swelling may be caused by bone knobs and/or hardened cartilage areas.

Victims of rheumatoid arthritis generally first start experiencing symptoms between the ages of 20 and 40, but children and elderly individuals may also experience the disease. Rheumatoid arthritis strikes chiefly the knuckle and wrist joints, but may occur in any joint. The disease frequently spreads throughout the body, damaging organs and connective tissue. If the disease is not stopped, the joints may ultimately stiffen in deformed positions. The disease may go into remission and then re-occur, or remain present during an individual's entire remaining lifetime.

During the progression of rheumatoid arthritis, inflamed tissue and other substances in the joint erode the cartilage and bone. In some cases an individual may inherit a tendency toward rheumatoid arthritis.

Other than osteoarthritis and rheumatoid arthritis, other common forms of arthritis include septic arthritis, ankylosing spondylitis, and gout. Septic arthritis involves an infection of a joint by bacteria. This form of arthritis frequently occurs following a lung or skin infection, any one of several venereal diseases, or joint surgery.

Ankylosing spondylitis causes spinal joints to become inflamed, leading to a rigid, curved back. Most ankylosing spondylitis victims are young men, many who are of the blood type HLA B-27, a relatively rare blood type.

Gout sufferers experience recurring flare-ups of painful joint swelling, but feel fine between attacks. In most cases, the joint between the big toe and the foot is first affected. This form of arthritis is caused by too much uric acid in the blood. During a gout attack, the uric acid manifests itself as sharp crystalline structures in the joint, leading to pain and swelling. It is believed that this form of arthritis may be inherited. Factors which may precipitate a gout attack include consumption of rich food and excessive drinking of alcoholic beverages.

Muscle pain is another affliction that affects large numbers of people each year. The muscle pain may be caused by over-exertion, injury, or even lack of exercise coupled with sudden action. Such muscle pain in some cases may be severe, and incapacitating to the afflicted individuals.

Dry skin is a problem which is especially pervasive in dry climates and elderly individuals. The symptoms of dry skin can include flaking, scaly skin, and itchiness. These types of symptoms affect many individuals each year.

Thus an urgent need exists for a remedy to alleviate the symptoms of arthritis, muscle pain, and dry skin. In view of the cost of many currently available ethical pharmaceuticals, it would be preferable to formulate a remedy which is made of natural ingredients, which are readily available off-the-shelf, and thus inexpensive.

In addition, many horses suffer from muscle pain and/or arthritis. Therefore, it would also be desirable to formulate a natural remedy which is capable of treating these afflictions in horses.

SUMMARY OF THE INVENTION

Accordingly, it is an object of the present invention to provide an arthritis, muscle pain, and dry skin remedy which alleviates the symptoms of arthritis in humans. Design features allowing this object to be accomplished include a mixture of rubbing alcohol, witch hazel, and virgin olive oil. Advantages associated with the accomplishment of this object include reduction of arthritis pain and swelling.

It is another object of the present invention to provide an arthritis, muscle pain, and dry skin remedy which treats muscle pain in humans. Design features allowing this object to be accomplished include a mixture of rubbing alcohol, witch hazel, and virgin olive oil. A benefit associated with the accomplishment of this object is alleviation of muscle pain in humans.

It is still another object of this invention to provide an arthritis, muscle pain, and dry skin remedy which relieves the symptoms of dry skin in humans. Design features enabling the accomplishment of this object include a mixture of rubbing alcohol, witch hazel, and virgin olive oil. An advantage associated with the realization of this object is alleviation of the symptoms of dry skin.

It is another object of the present invention to provide an arthritis, muscle pain, and dry skin remedy which may be used to treat muscle pain and/or in horses arthritis. Design features allowing this object to be accomplished include a mixture of rubbing alcohol, witch hazel, and castor oil. Benefits associated with the accomplishment of this object include alleviation of muscle pain and arthritis symptoms in horses.

It is still another object of this invention to provide an arthritis, muscle pain, and dry skin remedy which is made of naturally occurring ingredients. Design features enabling the accomplishment of this object include use of readily available materials such as rubbing alcohol, witch hazel, olive oil, and castor oil. Benefits associated with reaching this objective include reduced cost, and hence increased availability.

BRIEF DESCRIPTION OF THE DRAWINGS

The invention, together with the other objects, features, aspects and advantages thereof will be more clearly understood from the following in conjunction with the accompanying drawings.

Two sheets of drawings are provided. Sheet one contains FIG. 1. Sheet two contains FIG. 2.

FIG. 1 is a front isometric view of a bottle containing arthritis, muscle pain, and dry skin remedy which relieves symptoms in humans. The contents of the bottle have not yet been mixed together.

FIG. 2 is a front isometric view of a bottle containing an alternate embodiment of the instant arthritis, muscle pain, and dry skin remedy which relieves symptoms in horses. The contents of the bottle have not yet been mixed together.

DETAILED DESCRIPTION OF THE PREFERRED EMBODIMENT

FIG. 1 is a front isometric view of container 12 containing arthritis, muscle pain, and dry skin remedy 2 which relieves symptoms in humans. The contents of container 12 have not yet been mixed together. Arthritis, muscle pain, and dry skin remedy 2 for use by humans comprises rubbing alcohol 4, witch hazel 6, and olive oil 8. It has been determined experimentally that a solution containing sixteen (16) parts rubbing alcohol 4, sixteen (16) parts witch hazel 6, and four (4) parts olive oil 8 yields the best results. As a matter of production practicality, good results will be obtained if these quantities are used within a tolerance of ±two (2) parts for rubbing alcohol 4 and witch hazel 6, and ±one (1) part for olive oil 8.

When preparing arthritis, muscle pain, and dry skin remedy 2, the ingredients are placed together in a container 12 in the proper amounts, and then the ingredients are mixed by shaking the container 12. No special storage requirements exist other than keeping the container 12 away from flame or fire, or other excessive heat.

In use, the instant arthritis, muscle pain, and dry skin remedy 2 should be rubbed onto the afflicted individual's skin where symptoms exist five or six times a day, approximately every four (4) hours. Arthritis, muscle pain, and dry skin remedy 2 should never be rubbed onto the head of the patient above the neck. In addition, arthritis, muscle pain, and dry skin remedy 2 should never be taken internally. After the symptoms are relieved, arthritis, muscle pain, and dry skin remedy 2 should be applied once per day as a preventive measure.

In the preferred embodiment, the olive oil 8 used was virgin olive oil and the rubbing alcohol 4 was either clear or green rubbing alcohol. The witch hazel 6 used was of the type which is commonly available commercially, containing bark and leaves of a shrub of the Mamamelis genus (witch or wych hazel) in an alcoholic solution.

FIG. 2 is a front isometric view of a bottle containing an alternate embodiment of arthritis, muscle pain, and dry skin remedy 2, which relieves symptoms in horses. The contents of container 12 have not yet been mixed together. Arthritis, muscle pain, and dry skin remedy 2 for use by horses comprises rubbing alcohol 4, witch hazel 6, and castor oil 10. It has been determined experimentally that a solution containing sixteen (16) parts rubbing alcohol 4, sixteen (16) parts witch hazel 6, and four (4) parts castor oil 10 yields the best results. As a matter of production practicality, good results will be obtained if these quantities are used within a tolerance of ±two (2) parts for rubbing alcohol 4 and witch hazel 6, and ±one (1) part for castor oil 10.

When preparing the alternate embodiment arthritis, muscle pain, and dry skin remedy 2 depicted in FIG. 2, the ingredients are placed together in a container 12 in the proper amounts, and then the ingredients are mixed by shaking the container 12. No special storage requirements exist other than keeping the container 12 away from flame or fire, or other excessive heat.

In use, the instant arthritis, muscle pain, and dry skin remedy 2 should be rubbed onto the afflicted horse's skin where symptoms exist five or six times a day, approximately every four (4) hours. Arthritis, muscle pain, and dry skin remedy 2 should never be rubbed onto the head of the afflicted animal above the neck. In addition, arthritis, muscle pain, and dry skin remedy 2 should never be taken internally. After the symptoms are relieved, arthritis, muscle pain, and dry skin remedy 2 should be applied once per day as a preventive measure.

In the preferred embodiment, the castor oil 10 used was commercially available castor oil, and the rubbing alcohol 4 could be either clear or green rubbing alcohol. The witch hazel 6 used was of the type which is commonly available commercially, containing bark and leaves of a shrub of the Mamamelis genus (witch or wych hazel) in an alcoholic solution.

While a preferred embodiment of the invention has been illustrated herein, it is to be understood that changes and variations may be made by those skilled in the art without departing from the spirit of the appending claims.

| DRAWING ITEM INDEX | |
| --- | --- |
| 2 | arthritis, muscle pain, and dry skin remedy |
| 4 | rubbing alcohol |
| 6 | witch hazel |
| 8 | olive oil |
| 10 | castor oil |
| 12 | container |

I claim:

1. An arthritis, muscle pain, and dry skin remedy consisting essentially of sixteen (16) parts ±two (2) parts rubbing alcohol, sixteen (16) parts ±two (2) parts witch hazel and four (4) parts ±one (1) part olive oil.

2. The arthritis, muscle pain, and dry skin remedy of claim 1 wherein said olive oil is virgin olive oil.

3. The arthritis, muscle pain, and dry skin remedy of claim 2 wherein said rubbing alcohol is either green or clear rubbing alcohol.

4. An arthritis, muscle pain, and dry skin remedy consisting essentially of sixteen (16) parts ±two (2) parts rubbing alcohol, sixteen (16) parts ±two (2) parts witch hazel, and four (4) parts ±one (1) part castor oil.

5. The arthritis, muscle pain, and dry skin remedy of claim 4 wherein said rubbing alcohol is either green or clear rubbing alcohol.

* * * * *